United States Patent
Deppisch et al.

(10) Patent No.: US 6,387,132 B1
(45) Date of Patent: May 14, 2002

(54) ARTIFICIAL JOINT OF A PROSTHESIS

(75) Inventors: Werner Deppisch, deceased, late of Bischofswiesen, by Ursula Deppisch-Roth heir; Hans-Georg Pfaff, Ostfildern; Gerd Willmann, Leinfelden, all of (DE)

(73) Assignee: Ceramtec AG Innovative Ceramic Engineering, Plochingen (DE)

( * ) Notice: Subject to any disclaimer, the term of this patent is extended or adjusted under 35 U.S.C. 154(b) by 0 days.

(21) Appl. No.: 09/555,253

(22) PCT Filed: Nov. 30, 1998

(86) PCT No.: PCT/EP98/07709

§ 371 Date: Jul. 28, 2000

§ 102(e) Date: Jul. 28, 2000

(87) PCT Pub. No.: WO99/27871

PCT Pub. Date: Jun. 10, 1999

(30) Foreign Application Priority Data

Nov. 28, 1997 (DE) .......................... 197 52 674

(51) Int. Cl.⁷ ................................ A61F 2/30
(52) U.S. Cl. ................. 623/22.11; 623/23.56
(58) Field of Search .......... 623/16.11, 18.11, 623/22.11, 23.36, 23.56

(56) References Cited

U.S. PATENT DOCUMENTS

| 4,016,651 A | | 4/1977 | Kawahara et al. .......... 32/10 A |
| 4,155,124 A | * | 5/1979 | Kawahara et al. ....... 623/23.56 |
| RE32,449 E | * | 6/1987 | Claussen et al. ............. 501/103 |
| 4,950,294 A | * | 8/1990 | Hakamatsuka ........... 623/16.11 |
| 4,996,117 A | * | 2/1991 | Chu et al. .................... 428/633 |
| 5,168,080 A | * | 12/1992 | Suzuki ......................... 501/97 |
| 5,453,227 A | * | 9/1995 | Rieger ........................ 264/40.1 |
| 5,549,700 A | * | 8/1996 | Graham et al. ........... 623/22.11 |
| 5,562,738 A | * | 10/1996 | Boyd et al. ............... 623/17.11 |
| 5,677,014 A | * | 10/1997 | Ohnishi et al. ............. 427/555 |
| 5,916,498 A | * | 6/1999 | Hofmann et al. .............. 264/16 |
| 6,066,176 A | * | 5/2000 | Oshida ..................... 623/22.11 |

FOREIGN PATENT DOCUMENTS

DE 25 40 077 4/1976

OTHER PUBLICATIONS

H.J. Früh et al., "Wear characteristics of ceramic–on–ceramic for hip endoprostheses", Biomaterials, vol. 18, No. 12, pp. 873–876, 1997.

G. Willmann, "20 Jahre Aluminiumoxidkeramik für die Medizintechnik," (Alumina Ceramic Looks Back on 20 Years of Use in Medical Applications), Biomedizinische Technik, vol. 39, No. 4, Apr. 1, 1994, pp. 73–78.

* cited by examiner

Primary Examiner—Jeffrey A. Smith
Assistant Examiner—Michael B. Priddy
(74) Attorney, Agent, or Firm—Foley & Lardner

(57) ABSTRACT

Prostheses with artificial joints have only a few metallic and ceramic materials whose compatibility with human or animal tissue has been established. These materials, however, cannot be combined with one another in any manner if a friction pairing occurs as a result, for example, in the case of artificial joints. With artificial joints, joint partners are required to have good mechanical properties as well as tribological properties. According to the invention, a sintered material is thus provided which is comprised of zircon oxide with an addition of 0.1 to 40 wt. % aluminum oxide. This sintered material enables an artificial joint of a prosthesis whose other ceramic materials are comprised of aluminum oxide or zircon oxide with the given proportions of aluminum oxide to be assembled with joint partners.

14 Claims, 1 Drawing Sheet

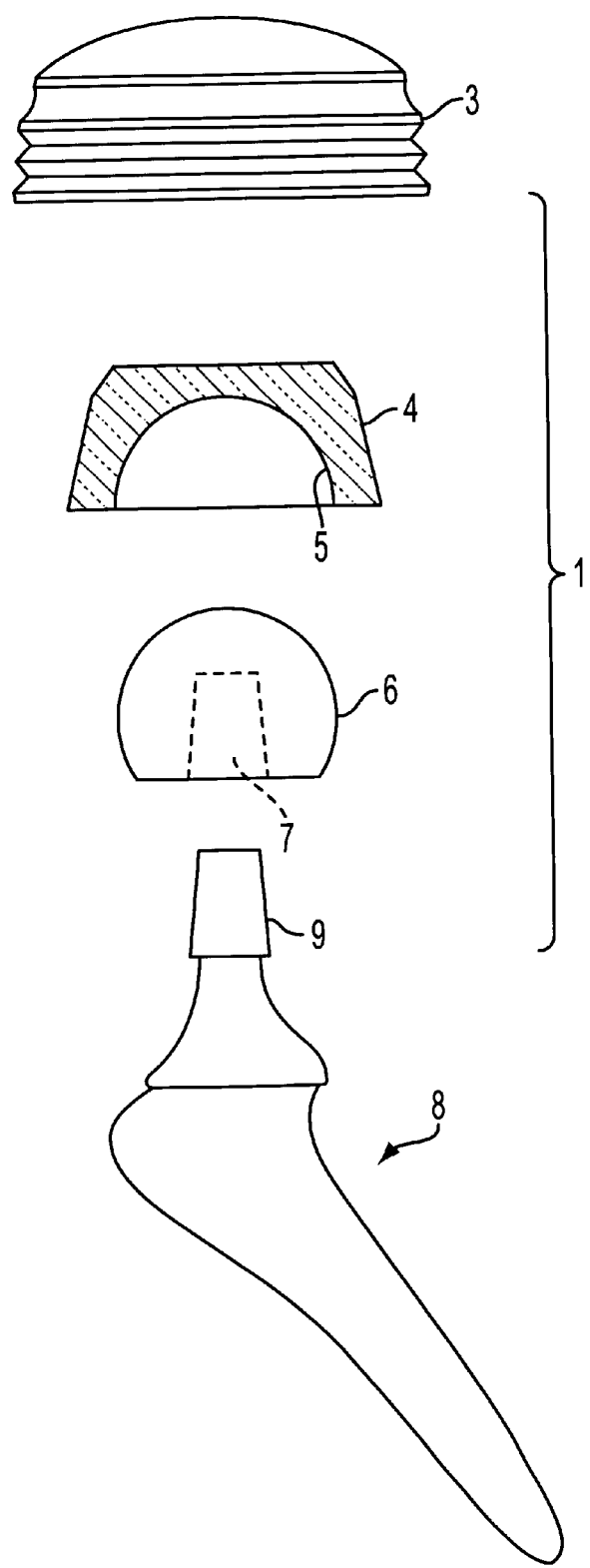
FIGURE

ARTIFICIAL JOINT OF A PROSTHESIS

BACKGROUND OF THE INVENTION

1. Field of the Invention

The invention relates to a ceramic sintered material for prostheses or implants and also to an artificial joint of a prosthesis, in which at least one joint partner consists of this ceramic material.

2. Description of the Related Art

It is only possible to use a few materials for prostheses with artificial joints on account of the compatibility that is required with human or even animal tissue, the so-called biocompatibility, and the high level of frictional loading of the joint partners. Of metallic materials, titanium-based alloys, for example TiAl6V4, TiAl6Nb7, and cobalt-chromium (CoCrMo) have proved good. Of plastics materials, in particular polyethylene is used for the sockets of the hip-joint endoprostheses and aluminium oxide and zirconium oxide are the ceramic materials that can be used. Whilst prostheses made of merely one of the materials that have been mentioned do not raise any problems in human or animal tissue, the materials cannot be combined together one with the other in an arbitrary manner if friction pairings result, as is the case in artificial joints. Moreover, the presence of the body fluid as a corrosive medium is to be taken into account.

In joints, pairings of joint partners of aluminium oxide, as is the case, for example, in hip-joint endoprotheses, have proved to be particularly good. Both the ball and the socket are made of the same ceramic material. As is known from the publication "Frettingkorrosion, ein Problem bei Hüftendoprothesen" by Früh, Willmann and Pfaff fErom "Biomaterials", 18 (1997), No. 12, pages 873 to 876, joint partners of aluminium oxide and of zirconium oxide cannot be paired together, because wear that cannot be tolerated occurs as a result. Even a pairing of joint partners of zirconium oxide is not possible on account of the wear.

It is however, possible to produce with zirconium-oxide ceramic materials work-pieces which, gives comparable dimensions, have a comparatively high level of reliability in particular against comparatively high alternating loads. For this reason, for example, it is not expedient to produce the ball-head diameters of hip-joint endoprostheses below 28 mm in diameter out of aluminium oxide. Diameters below 28 mm with the required levels of strength and endurance strength under alternating repetition of loads can, however, be realized in a problem-free manner with ceramic materials made from zirconium oxide. The disadvantage, however, lies in the fact that balls of zirconium-oxide ceramic material cannot be positioned against sockets made of aluminium oxide and zirconium oxide. It is therefore usual to position balls of zirconium oxide in sockets of polyethylene, although this causes particle-abrasion of polyethylene and thus results in medical problems.

SUMMARY OF THE INVENTION

The object of the present invention is therefore to put forward a material, and with that possible pairings of material, for prostheses with joint partners of ceramic materials, whereby new structural configurations with optimum wear characteristics are rendered possible.

According to one aspect of the present invention, there has been provided an artificial joint for a prosthesis, comprising (a) a first joint partner; and (b) a second joint partner cooperating with the first joint partner; wherein at least the first joint partner is made of a sintered material consisting essentially of zirconium oxide and 0.1 to 40% by weight aluminum oxide.

BRIEF DESCRIPTION OF THE DRAWINGS

The FIGURE diagrammatically shows component parts of a modularly constructed hip-joint endoprosthesis made of the material in accordance with the invention.

DETAILED DESCRIPTION OF PREFERRED EMBODIMENTS

The material in accordance with the invention made from zirconium oxide with an addition of 0.1 to 40% by weight aluminium oxide presents the possibility of realizing dimensions of the joint partners, for example the diameter of ball diameters of the hip-joint endoprostheses, that lie below 28 mm, in which case the good thermal and mechanical properties of the zirconium oxide are combined with time excellent tribological properties of the aluminium oxide.

The material in accordance with the invention renders possible pairings of materials in the case of artificial joints of prostheses that could not be realized before, for example, for reasons of wear.

Particularly good tribological properties, wear resistance, in conjunction with good thermal and mechanical characteristics, in particular little heating and high levels of endurance strength during alternating repetition of loads, are offered by a sintered material of zirconium oxide with an addition of 15 to 25% by weight aluminium oxide.

Stabilization of the zirconium-oxide phases is advantageously achieved if the proportion of the known stabilizers, for example rare earth oxides, alkaline earth oxides, titanium oxide, chromium oxide or hafnium oxide, lies below 10% by weight.

Furthermore, it is advantageous if both joint partners have the same material composition. As a result, the sliding partners are identical in terms of their abrasion characteristics. The resistance to wear increases with an increasing proportion of aluminium oxide.

It can, however, be thoroughly advantageous if one of the joint partners has a higher proportion of zirconium oxide than the other partner. This can be the case, for example, with the balls of the hip-joint endoprotheses in order to be able to utilize to the full the advantageous material properties of zirconium oxide, in particular with regard to the dimensions of the ball.

The material composition in accordance with the invention also makes it possible for one joint partner of zirconium oxide with a proportion of aluminium oxide of more than 5% by weight to be capable of being paired with a joint partner of pure aluminium oxide. As a result, the good tribological properties of the aluminium oxide can be utilized to the greatest possible extent.

The properties of the material composition can be utilized, in an advantageous manner, in an artificial hip joint, in which case the ball of the joint consists of the material with the predominant proportion of zirconium oxide. Since in particular the ball is the joint partner that is loaded to the greatest extent, with such a material composition the good tribological properties of the aluminium oxide are combined with the good thermal and mechanical properties of the zirconium oxide.

On account of the mechanical and thermal material properties of the zirconium oxide, it is possible, in an advantageous manner, to produce balls of hip-joint prostheses that have a diameter which is smaller than 28 mm and to pair them with a socket made of an aluminium-oxide ceramic material in order to render possible optimum wear characteristics.

Turning now to the FIGURE, the hip-joint and endoposthesis 1 consists of a two-part socket 2 which is anchored in the bone with its metallic socket housing 3 and accommodates a ceramic socket insert 4, in whose hollow sphere-shaped bearing surface 5 the ball 6 can move. The ball 6 also consists of ceramic material and has a conical core 7. The shaft 8, made of a bioinert metal, for example of the cobalt alloy CoCrMo, has a peg 9 whose conical form corresponds to the conical form of the bore 7 in the ball 6. The peg 9 is anchored in the bore 7 of the ball 6 by means of press fit.

In the present exemplifying embodiment, of the joint partners, the ball 6 and the socket inert 4, the ball 6 consists of zirconium oxide with a proportion of aluminium oxide of more than 5% by weight. The socket insert 4 consists of an aluminium-oxide ceramic material of known composition. The ball 6 has a diameter which is smaller than 28 mm. The material composition in accordance with the invention renders possible a substantially smaller diameter for the ball than is possible with a material of pure aluminium oxide. A ball that is of the specified material can be assembled, without risk, together with a socket insert of aluminium oxide to form a joint pairing, without the occurrence of any abrasive and corrosive damage.

What is claimed is:

1. An artificial joint for a prosthesis, comprising:
   (a) a first joint partner; and
   (b) a second joint partner cooperating with the first joint partner;
   wherein at least said first joint partner is made of a sintered material consisting essentially of zirconium oxide and 0.1 to 40% by weight aluminum oxide.

2. An artificial joint according to claim 1, wherein said sintered material of the first joint partner consists essentially of zirconium oxide and 15 to 25% by weight aluminum oxide.

3. An artificial joint according to claim 1, wherein said first joint further comprises less than 10% by weight of a stabilizer for the zirconium oxide phase.

4. An artificial joint according to claim 1, wherein both said first joint partner and said second joint partner are made of said sintered material.

5. An artificial joint according to claim 4, wherein one of said first and second joint partners comprises a higher proportion of zirconium oxide than the other of said first and second joint partners.

6. An artificial joint according to claim 1, wherein said second joint partner consists essentially of aluminum oxide and said first joint partner consists essentially of zirconium oxide with at least 5% by weight of aluminum oxide.

7. An artificial joint according to claim 1, wherein said joint comprises an artificial hip joint.

8. An artificial joint according to claim 7, wherein said second joint partner comprises a socket.

9. An artificial joint according to claim 8, wherein said first joint partner comprises a ball.

10. An artificial according to claim 9, wherein said ball is made of sintered material having a higher proportion of zirconium oxide than the sintered material of said socket.

11. An artificial joint according to claim 9, wherein a diameter of said ball is less than 28 mm.

12. An artificial joint according to claim 9, wherein only said material of said ball contains zirconium oxide.

13. An artificial joint according to claim 4, wherein both of said first and second joint members are made of sintered material having essentially the same composition.

14. An artificial joint according to claim 1, wherein said cooperation comprises rubbing contact.

* * * * *